United States Patent
Cho et al.

(10) Patent No.: US 10,202,321 B1
(45) Date of Patent: Feb. 12, 2019

(54) METHOD OF SIMULTANEOUSLY PREPARING 1,1,1-TRIFLUORO-2-CHLOROPROPENE AND 1,1,1,2-TETRAFLUOROPROPENE USING GAS PHASE CATALYST

(71) Applicant: FOOSUNG CO., LTD., Hwaseong-si, Gyeonggi-do (KR)

(72) Inventors: Ook Jae Cho, Ulsan (KR); Bong Seok Kim, Ulsan (KR); Dong Hyuk Park, Ulsan (KR); Su Jin Park, Ulsan (KR); Jin A Jung, Ulsan (KR); Dae Woo Kim, Ulsan (KR)

(73) Assignee: FOOSUNG CO., LTD. (KR)

( * ) Notice: Subject to any disclaimer, the term of this patent is extended or adjusted under 35 U.S.C. 154(b) by 0 days.

(21) Appl. No.: 15/970,703

(22) Filed: May 3, 2018

(30) Foreign Application Priority Data

Aug. 8, 2017 (KR) .......................... 10-2017-0100317

(51) Int. Cl.
| C07C 17/20 | (2006.01) |
| C07C 19/10 | (2006.01) |
| B01J 23/06 | (2006.01) |
| B01D 3/14 | (2006.01) |

(52) U.S. Cl.
CPC .............. *C07C 17/206* (2013.01); *B01D 3/14* (2013.01); *B01J 23/06* (2013.01); *C07C 19/10* (2013.01); *B01J 2208/00061* (2013.01); *B01J 2208/00539* (2013.01); *B01J 2208/00548* (2013.01)

(58) Field of Classification Search
CPC ......... C07C 17/25; C07C 21/18; C07C 19/10; C07C 17/10; C07C 19/08; C07C 17/357
See application file for complete search history.

(56) References Cited

U.S. PATENT DOCUMENTS

| 8,058,486 B2 | 11/2011 | Merkel et al. |
| 8,329,964 B2 | 12/2012 | Devic et al. |
| 8,389,779 B2 | 3/2013 | Avril et al. |
| 2011/0124930 A1* | 5/2011 | Smith ................... C07C 17/087 570/156 |
| 2012/0215037 A1* | 8/2012 | Sun .......................... C07C 17/25 570/157 |

(Continued)

FOREIGN PATENT DOCUMENTS

| JP | 2009227675 A | 10/2009 |
| WO | 2011139646 A2 | 11/2011 |
| WO | 2012099776 A1 | 7/2012 |

*Primary Examiner* — Jafar F Parsa
(74) *Attorney, Agent, or Firm* — Renaissance IP Law Group LLP

(57) ABSTRACT

Disclosed is a method of simultaneously preparing 1,1,1-trifluoro-2-chloropropene and 1,1,1,2-tetrafluoropropene, the method including i) a step of elevating a temperature of a reactor charged with a gas phase catalyst up to a reaction temperature; ii) a step of feeding 1,1,1-trifluoro-2,3-dichloropropane and 2-chloro-1,1,1,2-tetrafluoropropane into the reactor, the temperature of which has been elevated; iii) a step of performing dehydrochlorination while maintaining the temperature of the reactor; and iv) a step of performing washing and distillation after the dehydrochlorination. In accordance with the present disclosure, a high-efficient gas-phase process of continuously, simultaneously preparing 1,1,1-trifluoro-2-chloropropene and 1,1,1,2-tetrafluoropropene is provided.

8 Claims, 1 Drawing Sheet

(56) References Cited

U.S. PATENT DOCUMENTS

2012/0215038 A1* 8/2012 Sun .................. C07C 17/25
570/157
2012/0232317 A1   9/2012 Nappa \* cited by examiner

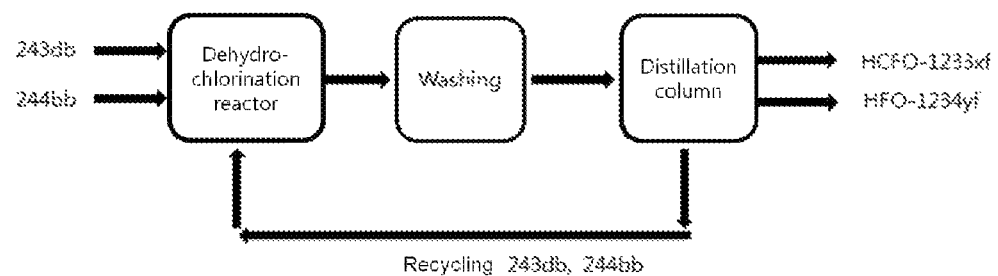

METHOD OF SIMULTANEOUSLY PREPARING 1,1,1-TRIFLUORO-2-CHLOROPROPENE AND 1,1,1,2-TETRAFLUOROPROPENE USING GAS PHASE CATALYST

CROSS-REFERENCE TO RELATED APPLICATION

This application claims priority to and the benefit of Korean Patent Application No. 2017-0100317, filed on Aug. 8, 2017, the disclosure of which is incorporated herein by reference in its entirety.

BACKGROUND

1. Technical Field

The present disclosure relates to a method of preparing 1,1,1-trifluoro-2-chloropropene and 1,1,1,2-tetrafluoropropene, and more particularly, to a method of simultaneously preparing 1,1,1-trifluoro-2-chloropropene and 1,1,1,2-tetrafluoropropene with high efficiency using the same gas phase catalyst and a single reactor.

2. Discussion of Related Art 1,1,1,2-tetrafluoropropene ($CF_3CF=CH_2$, 1234yf) is a promising new refrigerant for automobiles with low global warming potential. With regard to a method of preparing 1,1,1,2-tetrafluoropropene, a process of using 1,1,1,2,3,3-hexafluoropropene ($CF_3CF=CF_2$, HFP) as a raw material is known. As shown in [Reaction Scheme 1] below, a method of sequentially performing hydrogenation, dehydrofluorination, hydrogenation, and dehydrofluorination on HFP is mainly used. For example, U.S. Pat. No. 8,389,779 and U.S. Pat. No. 8,329,964 disclose a method of reacting 1,1,2,3,3,3(=1,1,1,2,3,3)-hexafluoropropylene (HFP) and hydrogen, as initial reactants, in the presence of a hydrogenation catalyst to generate 1,1,2,3,3,3(=1,1,1,2,3,3)-hexafluoropropylene (HFC-236ea), and then generating 1,2,3,3,3-pentafluoropropene (HFO-1225ye) through dehydrofluorination in the presence of a dehydrofluorination catalyst, followed by generating 1,2,3,3,3-pentafluoropropane (HFO-245eb) through a reaction with hydrogen in the presence of a hydrogenation catalyst, and then preparing 2,3,3,3-tetrafluoropropene (HFO-1234yf) through dehydrofluorination in the presence of a dehydrofluorination catalyst:

[Reaction Scheme 1]

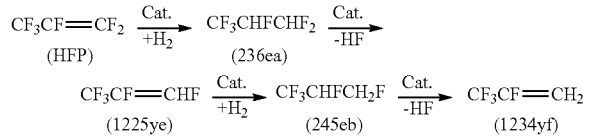

However, the HFO-1234yf preparation process represented by [Reaction Scheme 1] is disadvantageous in that HFP, as a raw material, is relatively expensive and about 5 to 10% of side reaction products are generated during a reaction process of 245eb to 1234yf.

In addition, Japanese Patent Application Publication No. 2009-227675 discloses a method of fluorinating a halopropane or halopropane, as a raw material, using hydrogen fluoride (HF), and WO2012/099776 discloses a method of preparing HFO-1234yf using 1,1,2,3-tetrachloropropene (HCO-1230xa) as a raw material.

Meanwhile, US Patent Application Publication No. 2012/0232317 discloses a method of preparing 1234yf through pyrolysis of 244bb ($CF_3CClFCH_3$) at a high reaction temperature of 460 to 620° C. without a catalyst. However, this method is disadvantageous in that the selectivity of 1234yf is decreased over reaction time due to the high reaction temperature. Such a problem was reported to be caused by fluorination and chlorination of a wall surface of a reactor.

In addition, International Patent Publication No. WO2011139646 discloses a method of preparing 1234yf through dehydrochlorination of 244bb ($CF_3CClFCH_3$) using a phase transfer catalyst (PTC) and KOH or NaOH under conditions such as a reaction temperature of 50° C. and a relatively high reaction pressure of 12 to 13 barg. However, this method requires a long reaction time and a process of processing KCl that is generated as a by-product, thus there is some difficulty in being commercially applied.

RELATED ART DOCUMENTS

Patent Documents

U.S. Pat. No. 8,389,779
U.S. Pat. No. 8,329,964
Japanese Patent Application Publication No. 2009-227675
International Patent Publication No. WO2012/099776
US Patent Application Publication No. 2012/0232317
International Patent Publication No. WO2011/139646

SUMMARY

Therefore, the present disclosure has been made in view of the above problems, and it is an objective of the present disclosure to provide an efficient method of simultaneously preparing 1,1,1-trifluoro-2-chloropropene and 1,1,1,2-tetrafluoropropene using the same gas phase catalyst in a single reactor.

In accordance with the present disclosure, the above and other objectives can be accomplished by the provision of a method of simultaneously preparing 1,1,1-trifluoro-2-chloropropene and 1,1,1,2-tetrafluoropropene, the method comprising: i) a step of elevating a temperature of a reactor charged with a gas phase catalyst up to a reaction temperature; ii) a step of feeding 1,1,1-trifluoro-2,3-dichloropropane and 2-chloro-1,1,1,2-tetrafluoropropane into the reactor, the temperature of which has been elevated; iii) a step of performing dehydrochlorination while maintaining the temperature of the reactor; and iv) a step of performing washing and distillation after the dehydrochlorination.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which:

FIG. 1 is a schematic diagram illustrating a process of simultaneously preparing 1,1,1-trifluoro-2-chloropropene and 1,1,1,2-tetrafluoropropene according to an embodiment of the present disclosure.

DETAILED DESCRIPTION OF EXEMPLARY EMBODIMENTS

Preferred embodiments of the present disclosure will now described more fully with reference to the accompanying drawings.

The present disclosure relates to a method of preparing 1234yf using 1,1,1,3-tetrachloropropane ($CCl_3CH_2CH_2Cl$, HCC-250fb) which is cheaper than 1,1,1,2,3,3-hexafluoropropene ($CF_3CF=CF_2$, HFP).

First, 1,1,1,3-tetrachloropropane ($CCl_3CH_2CH_2Cl$, HCC-250fb) may be prepared through a reaction between carbon tetrachloride ($CCl_4$) and ethylene ($CH_2=CH_2$) as shown in [Reaction Scheme 2]:

[Reaction Scheme 2]

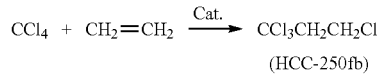

(HCC-250fb)

Here, one hydrogen, which is bonded to a middle carbon, should be substituted with a halogen (F, Cl, Br, I) so as to prepare HFO-1234yf using HCC-250fb as a starting material. This reaction is performed according to [Reaction Scheme 3] below:

[Reaction Scheme 3]

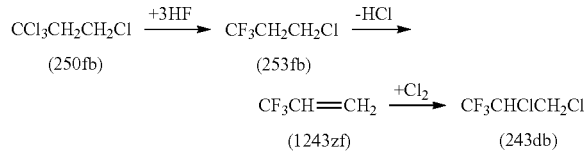

According to [Reaction Scheme 3], 3,3,3-trifluoropropene ($CF_3CH=CH_2$, 1243zf) may be prepared, and 1243zf is reacted with $Cl_2$ using a photoreactor to prepare 243db. According to [Reaction Scheme 4] below, 1233xf and 1234yf, as target materials of the present disclosure, may be obtained using 243db:

[Reaction Scheme 4]

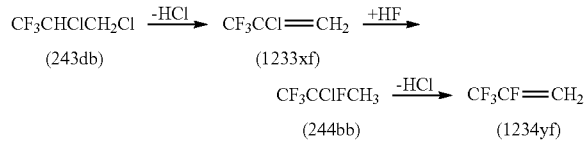

As shown in [Reaction Scheme 4], both a reaction of obtaining 1233xf from 243db and a reaction of obtaining 1234yf from 244bb are dehydrochlorination. Accordingly, the present inventors developed a method of preparing two products through a single reaction using the same catalyst, i.e., a method of providing a superior 243db conversion rate, superior 1234yf selectivity, and high process efficiency.

In particular, the method of simultaneously preparing 1,1,1-trifluoro-2-chloropropene and 1,1,1,2-tetrafluoropropene according to the present disclosure includes i) a step of elevating a temperature of a reactor charged with a gas phase catalyst up to a reaction temperature; ii) a step of feeding 1,1,1-trifluoro-2,3-dichloropropane and 2-chloro-1,1,1,2-tetrafluoropropane into the reactor, the temperature of which has been elevated; iii) a step of performing dehydrochlorination while maintaining the temperature of the reactor; and iv) a step of performing washing and distillation after the dehydrochlorination.

Here, the gas phase catalyst used for both the dehydrochlorination of 1,1,1-trifluoro-2,3-dichloropropane and the dehydrochlorination of 2-chloro-1,1,1,2-tetrafluoropropane is preferably a catalyst in which a metal is supported on a support. By using a support as described above, the life time of a catalyst is improved, and thus, there are advantages for commercial production. As examples of a support capable of being used in the present disclosure, there are activated carbon, activated alumina, a molecular sieve, and the like.

In addition, examples of the metal, which is supported on the support, capable of being used as a gas phase catalyst include Zn, Pd, Pt, Sb, V, Sn, Bi, and the like. It is further preferred to use Zn thereamong because a conversion rate of 243db and the selectivity of 1234yf are high during dehydrochlorination. In addition, when Zn content in the catalyst is 1 to 20% by weight, superior performance is exhibited. When the Zn content is less than 1%, catalytic activity is rapidly decreased. When the Zn content is 20% or more, there is a problem that a conversion rate is decreased.

When the catalyst is prepared, a first step of preparing 1,1,1-trifluoro-2-chloropropene and 1,1,1,2-tetrafluoropropene through dehydrochlorination according to the present disclosure, i.e., a step of charging a reactor with the gas phase catalyst, e.g., Zn/C, in which a metal is supported on a support and elevating a temperature, is performed. Here, since the dehydrochlorination is performed at about 300 to 400° C., a temperature of the reactor is elevated up to this temperature.

Subsequently, 1,1,1-trifluoro-2,3-dichloropropane and 2-chloro-1,1,1,2-tetrafluoropropane, as starting materials, are fed into the reactor heated to the reaction temperature. An inflow rate of 1,1,1-trifluoro-2,3-dichloropropane and 2-chloro-1,1,1,2-tetrafluoropropane introduced into the reactor is preferably 300 to 500 g/hr. When the raw materials are fed at 300 g/hr or less, there is a problem that a residence time is prolonged, and thus, a side reaction product is generated due to the high reaction temperature. When the raw materials are fed at 500 g/hr or more, a residence time is shortened, and thus, a conversion rate is decreased.

In addition, the temperature of an inlet, into which 1,1,1-trifluoro-2,3-dichloropropane and 2-chloro-1,1,1,2-tetrafluoropropane are introduced, is preferably 100 to 200° C. When the inlet temperature is 100° C. or less, the raw materials to be subjected to reaction are introduced into the reactor in a state in which the raw materials are not sufficiently vaporized in the inlet, and thus, the raw materials are vaporized in an upper part of the reactor, whereby it is difficult to maintain the temperature of the upper part of the reactor at the reaction temperature, i.e., 390° C. When the inlet temperature is too high, there is a problem that the raw materials themselves are partially decomposed in the inlet. Accordingly, it is preferred to install an electric preheater at the reactor inlet to maintain the inlet temperature within the range.

Meanwhile, an internal pressure of the reactor, in which dehydrochlorination is performed, is preferably atmospheric pressure to 0.1 barg. When the pressure of the reactor is high, boiling points of the raw materials increase, which may cause a problem that a high inlet temperature should be maintained upon supply of the raw materials.

As shown in FIG. 1, after completing dehydrochlorination in the reactor, a product is obtained through washing and distillation steps. 243db and 244bb, as raw materials, are simultaneously fed into a dehydrochlorination reactor, thereby simultaneously preparing 1233xf and 1234yf as products. Through this process, a by-product is generated along with the products. To remove HCl, the products are passed through a washing column, and then 1233xf and 1234yf are transferred to a distillation column. Using a first distillation column, 1234yf, as a final product having a low boiling point, is first distilled, and the distilled product is collected. Subsequently, using a second distillation column, 1233xf is distilled, and the distilled product is used as a raw material for preparing 244bb. In addition, unreacted raw materials, 243db and 244bb, are recovered from a distillation column and recycled to the dehydrochlorination reactor. Since unreacted 1,1,1-trifluoro-2,3-dichloropropane and 2-chloro-1,1,1,2-tetrafluoropropane are recycled to a dehydrochlorination reactor and thus are subjected to dehydrochlorination again as described above, the present disclosure may produce 1,1,1-trifluoro-2-chloropropene and 1,1,1,2-tetrafluoropropene in a more economical manner.

Hereinafter, the present disclosure will be described in detail by explaining particular examples of the disclosure. However, it should be understood that these examples are provided for illustrative purposes only and the scope of the present disclosure is not limited to the examples.

<Example 1> Dehydrochlorination of 243db

In Example 1, to investigate the reactivity of dehydrochlorination of 243db and 244bb, an experiment was carried out using a Zn/C catalyst. In particular, activated carbon was used as a support. 5 wt % Zn was supported on the support to be used as a reaction catalyst.

A 5 wt % Zn/C catalyst was prepared as described above, and a reactor manufactured with a 100 cm×2 inch Inconel pipe was charged with 1.6 L of the catalyst. Subsequently, an inner temperature of the reactor was sequentially elevated while flowing nitrogen at a rate of 5 L/min to dry the catalyst. The dried catalyst was used for the reaction. The reactor was stacked inside a heater to maintain the temperature of the reactor. In addition, the temperature of a middle part inside the reactor was monitored by means of a thermocouple.

After completing the drying of the catalyst, the reactor temperature was elevated up to 390° C., and then 243db, as a raw material, was passed through the catalyst at a flow rate of 500 g/hr. Here, for smooth feeding of the raw material, a 243db feed vessel was connected to a metering pump, and liquid-type 243db was fed into the reactor. In addition, for easy vaporization of 243db, an electric preheater was installed at an inlet of the reactor to maintain the temperature of the inlet at 200° C. Here, an internal pressure of the reactor was maintained at 0.1 barg.

Gas discharged from the reactor was periodically collected. To remove acidic gas from the collected gas, the collected gas was passed through an alkaline scrubber. The discharged gas was analyzed using GC-MS and GC. Reaction results are summarized in [Table 1] below.

TABLE 1

| Cat. | Reaction temperature (° C.) | 243db conversion rate (%) | 1233xf selectivity (%) |
|---|---|---|---|
| 5 wt % Zn/C | 390 | 93.18 | 89.5 |

<Example 2> Dehydrochlorination of 244bb

The reactor and catalyst used in Example 1 were used, and a catalyst was pre-treated and used in the same manner as in Example 1.

After completing the drying of the catalyst, the temperature was elevated up to a reaction temperature of 390° C., and then 244bb was passed through a catalyst layer at a rate of 300 g/hr. Here, for smooth feeding of 244bb as the raw material, a 244bb feed vessel was pre-heated to 50° C. so that 244bb in a gaseous form was fed into the reactor.

Gas discharged from the reactor was periodically collected. Acidic gas was removed from the collected gas in the same manner as in Example 1, followed by analysis using GC. Reaction results are summarized in [Table 2] below.

TABLE 2

| Cat. | Reaction temperature (° C.) | 244bb conversion rate (%) | 1234yf selectivity (%) |
|---|---|---|---|
| 5 wt % Zn/C | 390 | 77.21 | 88.10 |

<Example 3> Simultaneous Dehydrochlorination of 243db and 244bb

Under the same reaction conditions as in Examples 1 and 2, 243db and 244bb were simultaneously fed into a reactor, followed by performing dehydrochlorination. Here, 5 wt % Zn/C was used as a catalyst, and a reaction temperature was maintained at 390° C. The raw materials were fed at the following rates: 243db: 185 g/hr, and 244bb: 155 g/hr. The raw materials were passed through a catalyst layer.

A reacted and discharged gas was treated in the same manner as in Examples 1 and 2, and analyzed using GC. Reaction results are summarized in [Table 3] below

TABLE 3

| Cat. | Reaction temperature (° C.) | 243db conversion rate (%) | 244bb conversion rate (%) | 1233xf selectivity (%) | 1234yf selectivity (%) |
|---|---|---|---|---|---|
| 5 wt % Zn/C | 390 | 92.7 | 78.3 | 90.5 | 97.3 |

* 1234yf selectivity and 1233xf selectivity were calculated respectively based on 244bb and 243db.

It was confirmed that, when dehydrochlorination of 243db and 244bb was carried out using the same catalyst according to Example 3, the selectivity of 1234yf was increased. From this result, it can be considered that 1233xf, as a product of 243db, generated through the reaction has an effect of suppressing the generation of 1233xf in a process of producing 1234yf from 244bb, whereby the selectivity of 1234yf, as final product, is improved. As such, the present disclosure provides a gas phase process of simultaneously preparing 1233xf and 1234yf with high efficiency in a continuous process by dehydrochlorinating 243db and 244bb using the same catalyst in a single reactor.

As described above, the present disclosure provides a method of simultaneously preparing 1,1,1-trifluoro-2-chloropropene and 1,1,1,2-tetrafluoropropene using the same gas phase catalyst in a single reactor. The method is advantageous in that a conversion rate of 234db and the selectivity of 1234yf are superior and the provision of a commercially available high-efficient continuous process is possible.

It will be apparent to those skilled in the art that various modifications can be made to the above-described exemplary embodiments of the present disclosure without departing from the spirit or scope of the disclosure. Thus, it is intended that the present disclosure covers all such modifications provided they come within the scope of the appended claims and their equivalents.

What is claimed is:

1. A method of simultaneously preparing 1,1,1-trifluoro-2-chloropropene and 1,1,1,2-tetrafluoropropene, the method comprising:
    i) elevating a temperature of a reactor charged with a gas phase catalyst up to a reaction temperature;
    ii) feeding 1,1,1-trifluoro-2,3-dichloropropane and 2-chloro-1,1,1,2-tetrafluoropropane into the reactor, the temperature of which has been elevated;
    iii) performing dehydrochlorination while maintaining the temperature of the reactor; and
    iv) performing washing and distillation after the dehydrochlorination: and
    wherein the gas phase catalyst is a catalyst in which a metal is supported on a support, the support is selected from activated carbon, activated alumina, or a molecular sieve, and the metal is selected from the group consisting of Zn, Pd, Pt, Sb, V, Sn, and Bi.

2. The method according to claim 1, wherein the metal is Zn.

3. The method according to claim 2, wherein a Zn content in the gas phase catalyst is 1 to 20% by weight.

4. The method according to claim 1, wherein a reaction temperature of the reactor is 300 to 400° C.

5. The method according to claim 1, wherein an inflow rate of 1,1,1-trifluoro-2,3-dichloropropane and 2-chloro-1,1,1,2-tetrafluoropropane introduced into the reactor is 300 to 500 g/hr.

6. The method according to claim 1, wherein a temperature of an inlet, into which the 1,1,1-trifluoro-2,3-dichloropropane and the 2-chloro-1,1,1,2-tetrafluoropropane are introduced, is 100 to 200° C.

7. The method according to claim 1, wherein an internal pressure of the reactor is atmospheric pressure to 0.1 barg.

8. The method according to claim 1, wherein the distillation is performed in a distillation column, wherein unreacted 1,1,1-trifluoro-2,3-dichloropropane and 2-chloro-1,1,1,2-tetrafluoropropane in the distillation column are recycled to a dehydrochlorination reactor.

* * * * *